(12) United States Patent
Elku et al.

(10) Patent No.: US 9,895,457 B2
(45) Date of Patent: Feb. 20, 2018

(54) RADIATION LAMP AND RADIATION SOURCE MODULE INCORPORATING SAME

(75) Inventors: Joseph Elku, Tilsonburg (CA); Jim Fraser, St. Thomas (CA); Michael Sasges, Victoria (CA); Michael D. Rodgers, Waterloo (CA)

(73) Assignee: TROJAN TECHNOLOGIES, London (CA)

( * ) Notice: Subject to any disclaimer, the term of this patent is extended or adjusted under 35 U.S.C. 154(b) by 256 days.

(21) Appl. No.: 12/094,774

(22) PCT Filed: Nov. 22, 2006

(86) PCT No.: PCT/CA2006/001898
§ 371 (c)(1),
(2), (4) Date: Apr. 18, 2011

(87) PCT Pub. No.: WO2007/059609
PCT Pub. Date: May 31, 2007

(65) Prior Publication Data
US 2011/0227473 A1    Sep. 22, 2011

Related U.S. Application Data

(60) Provisional application No. 60/738,581, filed on Nov. 22, 2005.

(51) Int. Cl.
*H01R 33/06* (2006.01)
*H01R 13/02* (2006.01)
(Continued)

(52) U.S. Cl.
CPC ............... *A61L 2/10* (2013.01); *C02F 1/325* (2013.01); *H01J 5/60* (2013.01); *H01K 1/465* (2013.01);
(Continued)

(58) Field of Classification Search
CPC .......... F21V 19/006–19/0095; F21V 19/0065; F21V 19/0085; H01R 33/975–33/9756;
(Continued)

(56) References Cited

U.S. PATENT DOCUMENTS 2,259,378 A * 10/1941 Heidkamper ...... H01R 33/0845
439/244
2,336,587 A * 12/1943 Bixby ................ H01R 33/0836
362/217.08
(Continued)

FOREIGN PATENT DOCUMENTS

CN    1136855 A    11/1996
CN    101228606 A    7/2008
(Continued)

OTHER PUBLICATIONS

International Search Report in the corresponding International Application No. PCT/CA2006/001898.
(Continued)

*Primary Examiner* — Mariceli Santiago
(74) *Attorney, Agent, or Firm* — Katten Muchin Rosenman LLP

(57) ABSTRACT

A lamp device is disclosed. The lamp device comprises a first electrical connector and a second electrical connector located at a first end portion of the lamp device. The first end portion of the lamp device is received in a receptacle of a first base portion. A first locking portion is included for securing the first base portion to the first end portion. The present radiation lamp device obviates or mitigates the need to use adhesive and/or polymer insulation/O-rings to achieve electrical connections. Further, the present radiation lamp may be oriented in a vertical orientation without the need to use springs and/or rubber part to support the distal end of the lamp.

22 Claims, 26 Drawing Sheets

(51) Int. Cl.
- *H01J 5/60* (2006.01)
- *A61L 2/10* (2006.01)
- *C02F 1/32* (2006.01)
- *H01K 1/46* (2006.01)
- *H01R 33/94* (2006.01)
- *H01R 13/627* (2006.01)

(52) U.S. Cl.
CPC .......... *H01R 33/06* (2013.01); *H01R 33/942* (2013.01); *C02F 2201/004* (2013.01); *H01R 13/6273* (2013.01)

(58) Field of Classification Search
CPC ... H01R 33/97–33/973; H01R 33/7657; H01R 33/02–33/09; H01J 9/003; H01J 9/006; H01J 5/50–5/62
USPC ......... 313/243; 439/336–337, 235, 239–240, 439/242, 280, 375, 414, 419, 435
See application file for complete search history.

(56) References Cited

U.S. PATENT DOCUMENTS

| | | | | |
|---|---|---|---|---|
| 3,417,364 A | * | 12/1968 | Kunkle | H01R 33/97 439/233 |
| 3,466,594 A | * | 9/1969 | Detch | F21V 19/008 439/233 |
| 3,723,945 A | * | 3/1973 | Detch | F21V 19/008 362/217.08 |
| 3,729,700 A | | 4/1973 | Johnson et al. | |
| 3,818,418 A | * | 6/1974 | Detch | H01R 33/02 439/232 |
| 4,700,101 A | | 10/1987 | Ellner et al. | |
| 4,713,019 A | | 12/1987 | Gaynor | |
| RE32,624 E | | 3/1988 | Myles et al. | |
| 4,799,896 A | | 1/1989 | Gaynor et al. | |
| 5,166,527 A | | 11/1992 | Solymar | |
| 5,422,487 A | * | 6/1995 | Sauska | C02F 1/325 250/436 |
| 5,646,473 A | | 7/1997 | Eggink et al. | |
| 5,753,996 A | * | 5/1998 | Csoknyai | H01J 9/003 210/748.09 |
| 6,183,310 B1 | * | 2/2001 | Shu | F21S 4/001 439/699.2 |
| 6,340,310 B2 | * | 1/2002 | Henrici et al. | 439/346 |
| 6,838,057 B2 | * | 1/2005 | Russell | A61L 9/18 250/455.11 |
| 6,884,103 B1 | * | 4/2005 | Kovacs | 439/336 |
| 8,167,654 B2 | | 5/2012 | Elku et al. | |

FOREIGN PATENT DOCUMENTS

| | | |
|---|---|---|
| EP | 1 577 989 A1 | 9/2005 |
| GB | 518 204 | 2/1940 |
| GB | 533 451 | 2/1941 |
| WO | 98/46933 A2 | 10/1998 |

OTHER PUBLICATIONS

Office Action for Canadian Patent Application 3,630,609, dated Sep. 20, 2010.
Supplementary European Search Report for European Patent Application No. 06 80 4756, dated Aug. 19, 2010.
The First Office Action for Chinese Patent Application No. 200680043393.8, dated Dec. 25, 2009.
The Second Office Action for Chinese Patent Application No. 200680043393.8, dated Oct. 28, 2010.
The Third Office Action for Chinese Patent Application No. 200680043393.8, dated May 24, 2011.
Apr. 9, 2013 Office Action for Canadian Patent Application No. 2,630,609.
Mar. 19, 2014 Office Action for Canadian Patent Application No. 2,630,609.
Mar. 14, 2016 Office Action for Canadian Patent Application No. 2,630,609.
Feb. 20, 2013 Communication pursuant to Article 94(3) EPC for European Patent Application No. 06 804 756.2.
The First Office Action and an English translation for Chinese Patent Application No. 201210097732.8 dated May 6, 2014.
The Second Office Action and an English translation for Chinese Patent Application No. 201210097732.8 dated Jan. 21, 2015.

* cited by examiner

RADIATION LAMP AND RADIATION SOURCE MODULE INCORPORATING SAME

FIELD OF THE INVENTION

In one of its aspects, the present invention relates to a lamp device. In another of its aspects, the present invention relates to a radiation lamp. In yet another of its aspects, the present invention relates to a radiation source assembly. In yet another of its aspects, the present invention relates to a radiation source module. In yet another of its aspects, the present invention relates to a fluid treatment system. In yet another of its aspects, the present invention relates to a water disinfection system.

DESCRIPTION OF THE PRIOR ART

Fluid treatment systems such as water disinfection systems are generally known in the art.

See, for example, one or more of the following U.S. Pat. Nos.:
Re36,896,
3,418,370,
4,482,809,
4,872,980,
5,006,244,
5,471,063,
5,504,355,
5,538,210,
6,342,188,
6,500,346,
6,507,028,
6,646,269,
6,674,084,
6,803,586, and
6,863,078.

Many of the above-identified United States patents teach fluid treatment systems that employ ultraviolet (UV) radiation to kill, sterilize and/or prevent replication of microorganisms (bacteria, viruses, pathogens and the like) that may be present in the fluid.

Generally, such prior art fluid treatment systems employ an ultraviolet radiation lamp to emit radiation of a particular wavelength or range of wavelengths (usually between 185 and 400 nm) to kill, sterilize and/or prevent replication of microorganisms (bacteria, viruses, pathogens and the like) that may be present in the fluid.

Conventional ultraviolet radiation lamps include low pressure lamps, medium pressure lamps, low pressure high output lamps and the like.

In more recent years, it has become conventional to use such ultraviolet lamps configured to have all of the electrical connections disposed at one end of the lamp. See, for example, FIGS. 2-8 of U.S. Pat. No. 4,700,101 [Ellner et al. (Ellner)] and FIGS. 1, 2 and 4 of U.S. Pat. No. 5,166,527 [Solymar].

As can be seen from the prior art radiation lamps taught by Ellner, Solymar and others, it is conventional in the art to utilize so-called electrical pins at one end of the lamp. Typically, a ceramic base is used to cover the pinch of the lamp and the electrical pins emanate from the ceramic base. Another ceramic base is used to cover the pinch of the lamp at the opposite end (i.e., where there are no electrical pins emanating from the lamp. It is conventional to secure such ceramic (or similar) bases to the pinch of the lamp using an adhesive.

Unfortunately, the use of such adhesives to secure the ceramic bases to the pinch ends of the lamp often results in off-gas production from the adhesive thereby causing fouling on the inside of the quartz sleeve thus reducing radiation (e.g., ultraviolet radiation) output to the fluid (e.g., water) being treated. Further, the use of such adhesives can lead to stress cracking of the quartz pinch area of the lamp when the lamp is operated at relatively high temperature and/or during curing of the adhesive. Still further, from an engineering perspective, it is difficult to achieve reliable bonding using such adhesives.

It has also been conventional in the art of such lamps having electrical connections at a single end to utilize insulated return wires (e.g., insulated with a polymer such as Teflon) and polymer O-rings (e.g., Teflon O-rings) to hold the return wires in place along the lamp. If the polymer O-rings are omitted, a further problem can be created, namely that the wires can become non-aligned potentially blocking a radiation sensor element and/or creating short circuit (if non-insulated wires are used).

Unfortunately, the use of polymer (e.g., Teflon) insulation on the return wires and the O-rings often results in off-gas production thereby causing fouling on the inside of the quartz sleeve thus reducing radiation (e.g., ultraviolet radiation) output to the fluid (e.g., water) being treated.

In prior art, it is known to dispose ultraviolet radiation lamps vertically in a fluid treatment system. Such lamps are disposed in a protective quartz sleeve having an open end from which the lamp connections emanate and a closed (or domed) end. In such configurations, it is convention to utilize springs and/or rubber parts in the closed (or domed) end of the sleeve to support the lamp when installed vertically, thereby obviating undue stress on the electrical connection. Further, conventional such springs/and or rubber parts work best when the lamp is fully installed. There is a risk of partial or full disconnection of the electrical connection during installation and/or removal of the lamp.

Accordingly, there remains a need in the art for a radiation lamp device in which the need to use adhesive and/or polymer insulation/O-rings is obviated or mitigated. Further, there is a need in the art for an arrangement that allows for disposition of a radiation lamp in a vertical orientation without the need to use springs and/or rubber part to support the distal end of the lamp. Still further, there is a need in the art for a radiation lamp device that obviates or mitigates the problem of partial or full disconnection of the electrical connection described above.

SUMMARY OF THE INVENTION

It is an object of the present invention to obviate or mitigate at least one of the above-mentioned disadvantages of the prior art.

Accordingly, in one of its aspects, the present invention provides a lamp device comprising: (i) a first electrical connector and a second electrical connector located at a first end portion of the lamp device, (ii) a first base portion having a first receptacle for receiving the first end portion, and (iii) a first locking portion for securing the first base portion to the first end portion.

In another of its aspects, the present invention relates to a radiation source assembly comprising such a lamp device, together with a radiation transparent protective sleeve.

In another of its aspects, the present invention provides a radiation lamp comprising: an elongate radiation-emitting cavity having a longitudinal axis; a first electrical connection base disposed at a first end of the elongate radiation-emitting cavity; a second electrical connection base disposed at a second end of the elongate radiation-emitting cavity; a first elongate electrical connector and a second elongate electrical connector disposed in the first electrical connection base; an electrical lead electrically connecting one of the first elongate electrical connector and a second elongate electrical connectors to the second electrical connection base; and a tensioning element disposed on at least one of the first electrical connection base and the second electrical connection base, the tensioning element being configured to apply tension to the electrical lead between the first electrical connection base and the second electrical connection base.

In yet another of its aspects, the present invention provides a lamp device comprising: (i) a first elongate electrical connector and a second elongate electrical connector located at a first end portion of the lamp device, and (ii) a first base portion comprising a first element and a second element configured to be engageable to one another to secure the first base portion to the first end portion.

In yet another of its aspects, the present invention provides a radiation lamp comprising: an elongate radiation-emitting cavity having a longitudinal axis; a first connection base disposed at a first end of the elongate radiation-emitting cavity; a second connection base disposed at a second end of the elongate radiation-emitting cavity; a connection member interconnecting the first connection base and the second connection base; and a tensioning element disposed on at least one of the first connection base and the second connection base, the tensioning element being configured to apply tension to the connection member to secure at least one of the first electrical connection base and the second electrical connection base with respect to the elongate radiation-emitting cavity Other aspects of the present invention relate to fluid treatment systems and water disinfection systems incorporating the above lamp device, radiation source assembly, radiation lamp and radiation source module, respectively.

The present radiation lamp device obviates or mitigates the need to use adhesive and/or polymer insulation/O-rings to achieve electrical connections. Further, the present radiation lamp may be oriented in a vertical orientation without the need to use springs and/or rubber part to support the distal end of the lamp.

BRIEF DESCRIPTION OF THE DRAWINGS

Embodiments of the present invention will be described with reference to the accompanying drawings, wherein like reference numerals denote like parts, and in which.

DETAILED DESCRIPTION OF THE PREFERRED EMBODIMENTS

Figure 1:
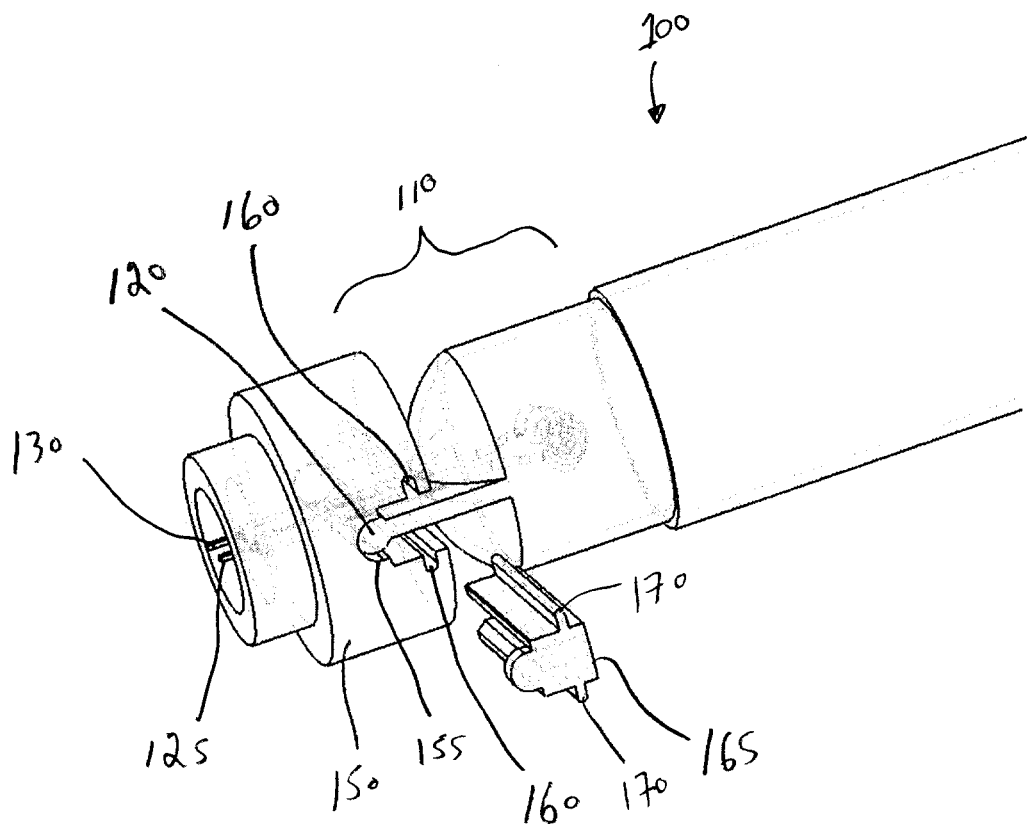
FIGS. 1 and 2 illustrate a perspective view of a first embodiment of the present lamp device.
Figure 2:
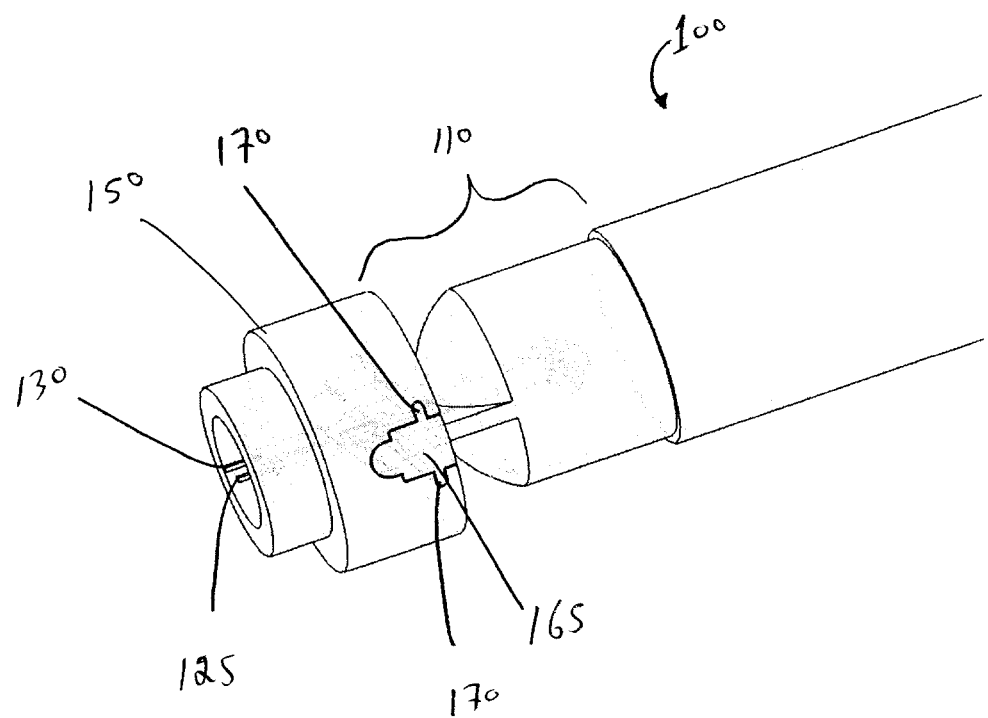
Figure 3:
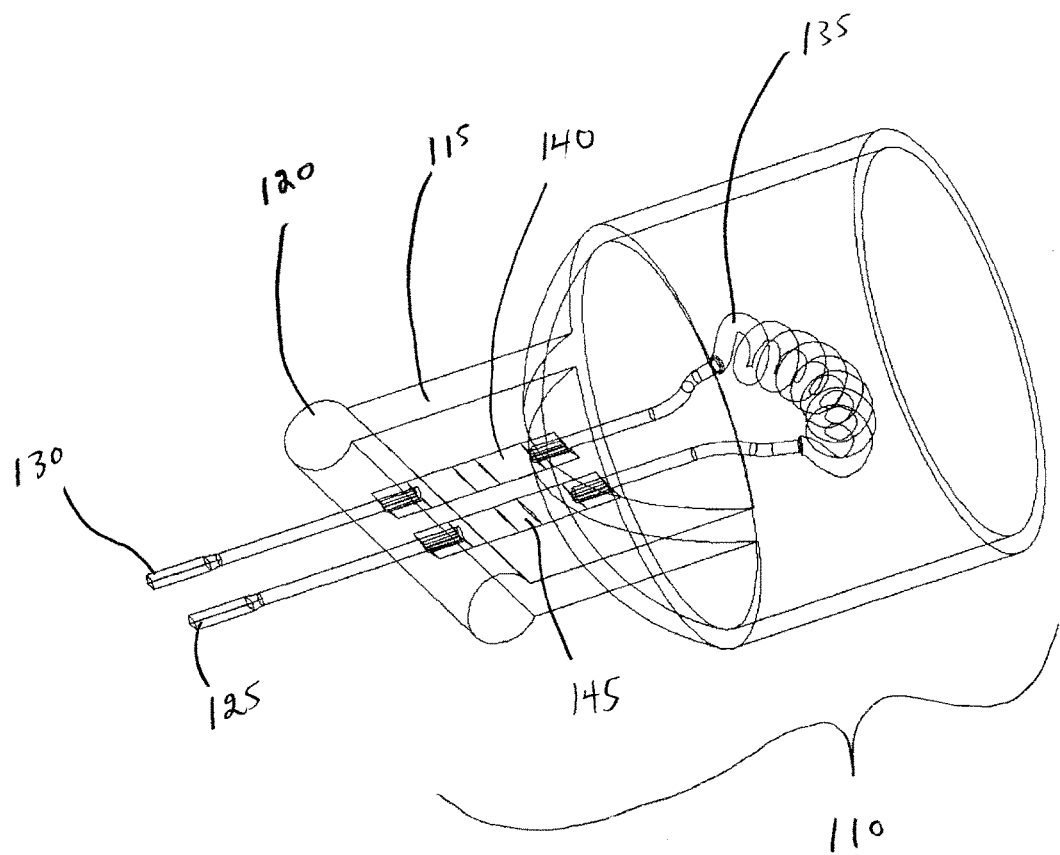
FIG. 3 illustrates an enlarged perspective view of a portion of the lamp in FIGS. 1 and 2 that has been ghosted.

With reference to FIGS. 1-3, there is illustrated a portion of a lamp device 100.

Lamp device 100 comprises an end portion 110. In the illustrated embodiment, end portion 110 comprises a pinch section 115 having a bulb 120 at one end thereof. Pinch section 115 interconnects a pair of electrical pins 125,130 to a filament 135 via a pair of electrical strips 140,145.

With reference to FIG. 1, a base portion 150 is provided having a large receptacle 155 and a pair of small receptacles 160.

With further reference to FIG. 1, there is a provided a key member 165 having a pair of tongues 170.

When it is desired to secure base member 150 to end portion 110 of lamp 100, bulb portion 120 is disposed in receptacle 155 of base member 150. Next, key element 165 is positioned such that tongues 170 are aligned with receptacles 160. Key element 165 is then pushed into place resulting in a secured connection of base member 150 to end region 110 of lamp 100—see FIG. 2.

Figure 4:
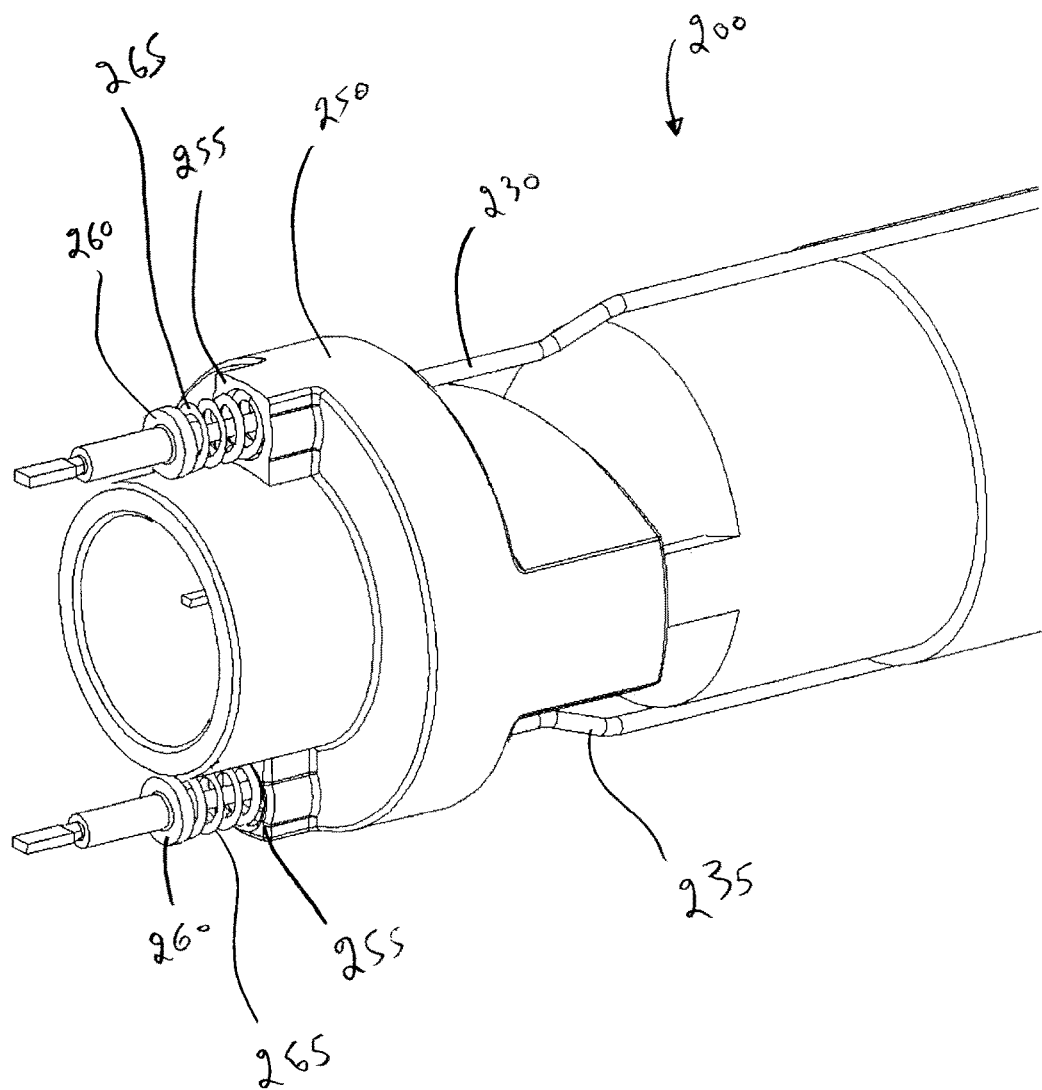
FIG. 4 illustrates a perspective view of a second embodiment of the present lamp device.
Figure 5:
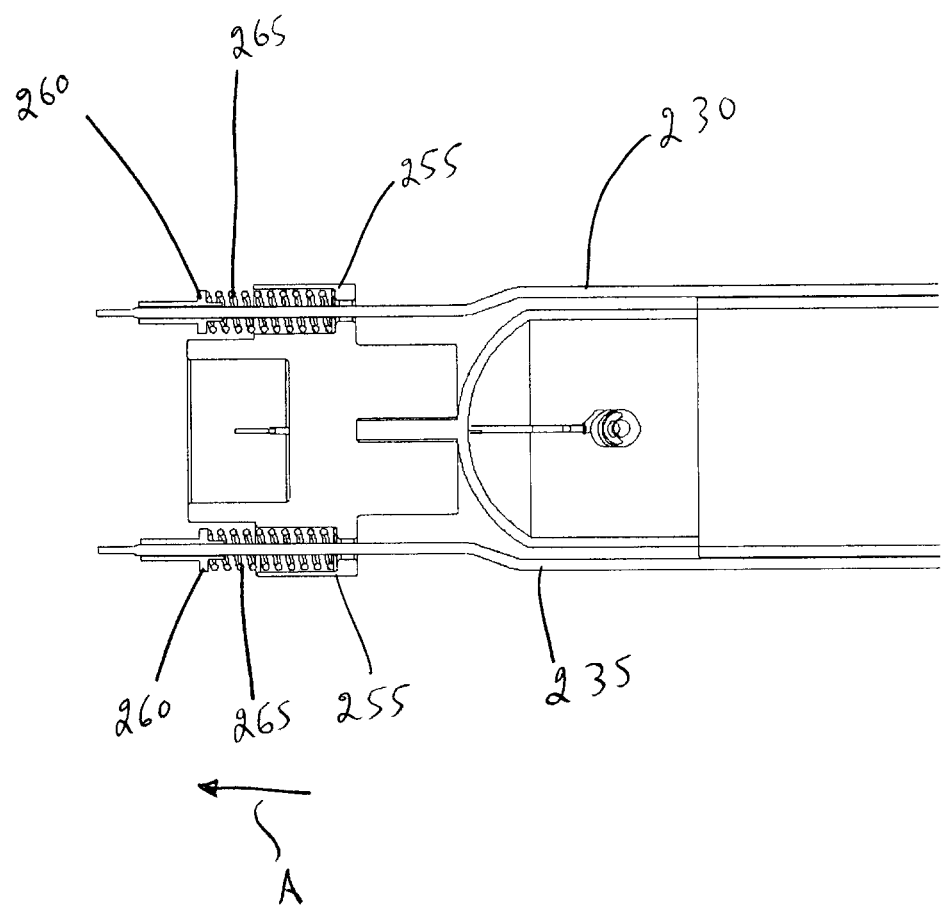
FIG. 5 illustrates a sectional view of the embodiment shown in FIG. 4.
Figure 6:
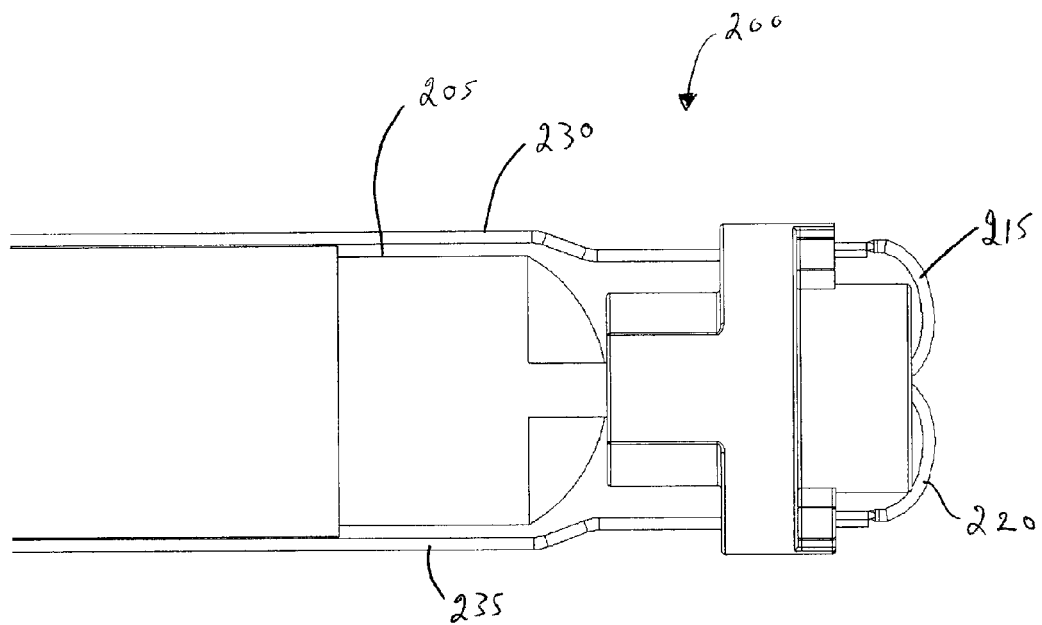
FIG. 6 illustrates a side elevation of the opposite end of the lamp shown in FIGS. 4 and 5.
Figure 7:
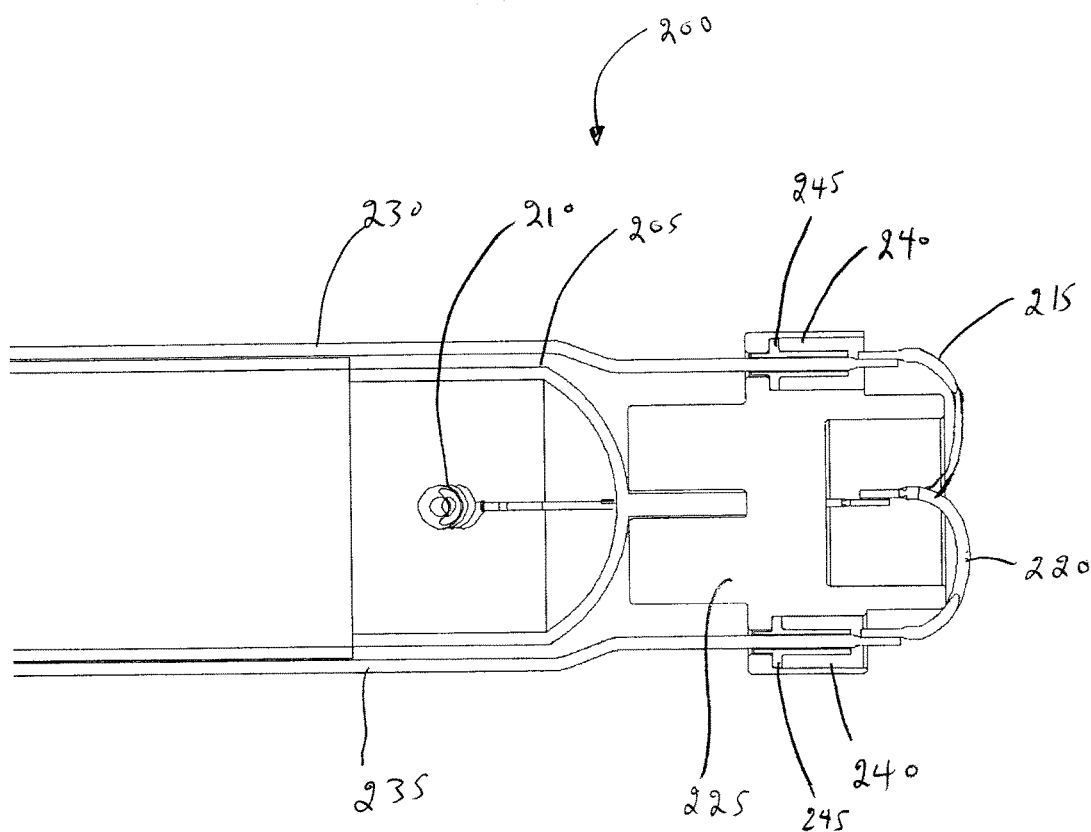
FIG. 7 illustrates a sectional view of the lamp shown in FIG. 6.
Figure 8:
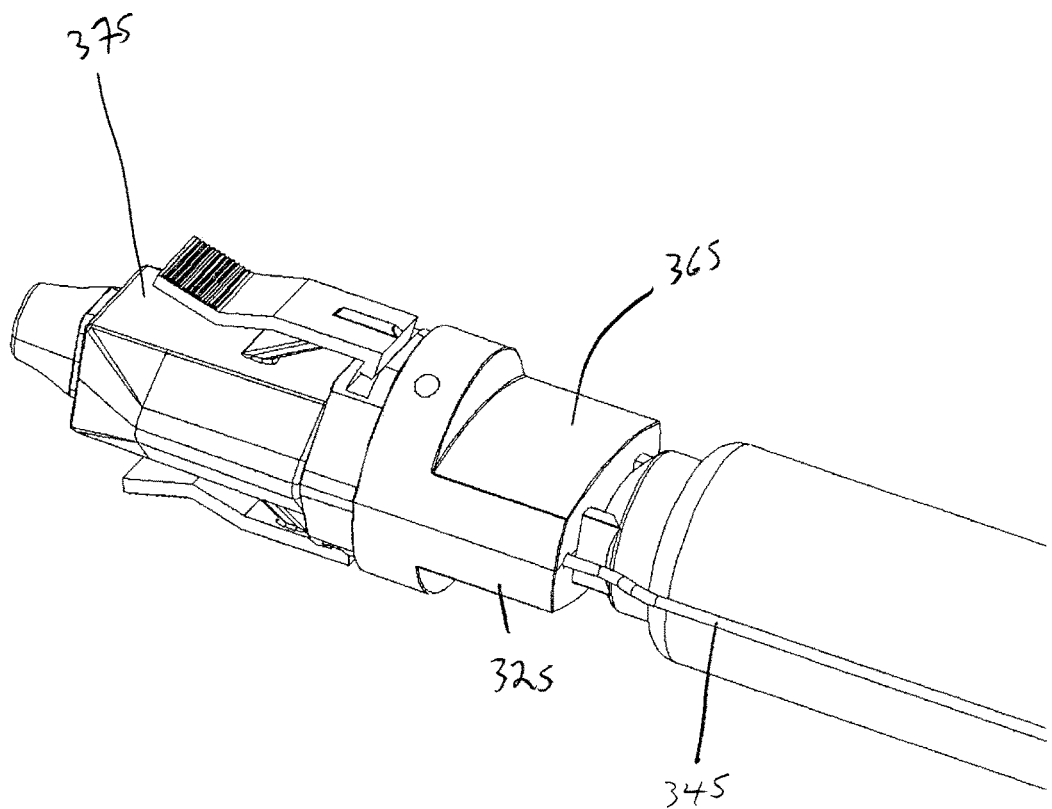
FIGS. 8-15 illustrate a third embodiment of the present lamp device.

With reference to FIGS. 4-7, there is illustrated a second embodiment of the present lamp device. Specifically, lamp device 200 comprises all of its electrical connections at one end of the lamp only. FIGS. 4 and 5 illustrate the end of lamp 200 containing the exposed electrical connections whereas FIGS. 6 and 7 illustrate the end of lamp 200 containing the return electrical connections.

With initial reference to FIGS. 6 and 7, there is shown a portion of radiation lamp emitting cavity 205 having disposed therein a filament 210. Filament 210 comprises a pair of electrical connections that are connected to a pair of electrical leads 215,220 via a conventional base element 225.

Electrical lead 215 is connected to a return wire 230 and electrical lead 220 is connected to a return wire 235.

Base element 225 comprises a pair of receptacles 240 each of which receive an end portion of return wires 230,235. Each of return wires 230,235 has crimped (or otherwise secured thereto) a stop member 245 which serves to abut against the walls of receptacle 240 of base element 225.

With reference to FIGS. 4 and 5, return wires 230,235 are shown passing through base element 250. Preferably, base element 250 is similar to base element 150 described above with reference to FIGS. 1-3; base element 250 is modified to include a pair of receptacles 255 through which return wires 230,235 pass.

Crimped (or otherwise secured to) the ends of return wires 230,235 is a stop member 260. Disposed between stop member 260 and receptacle 255 is a spring 265.

Spring 265 is chosen to impart tension on return wires 230,235 in the direction of Arrow A (FIG. 5). The conveyance of such tension to return wires 230,235 serves to compensate for thermal expansion of the wires while eliminating stress on the electrical connections at the distal end of the lamp.

With reference to FIGS. 8-15, there is illustrated a third preferred embodiment of the present lamp device shown with a plug connector (FIGS. 8-12).

Figure 13:
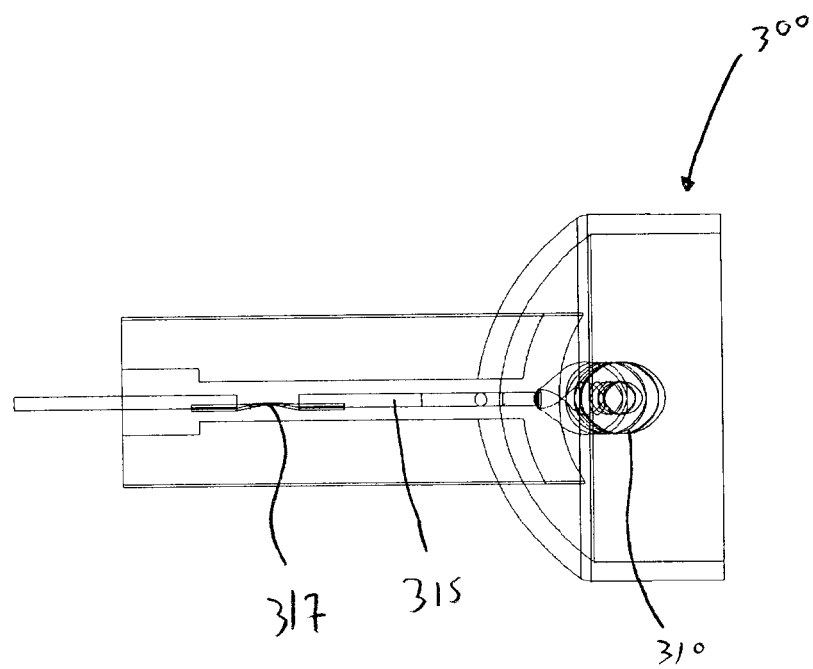
Figure 14:
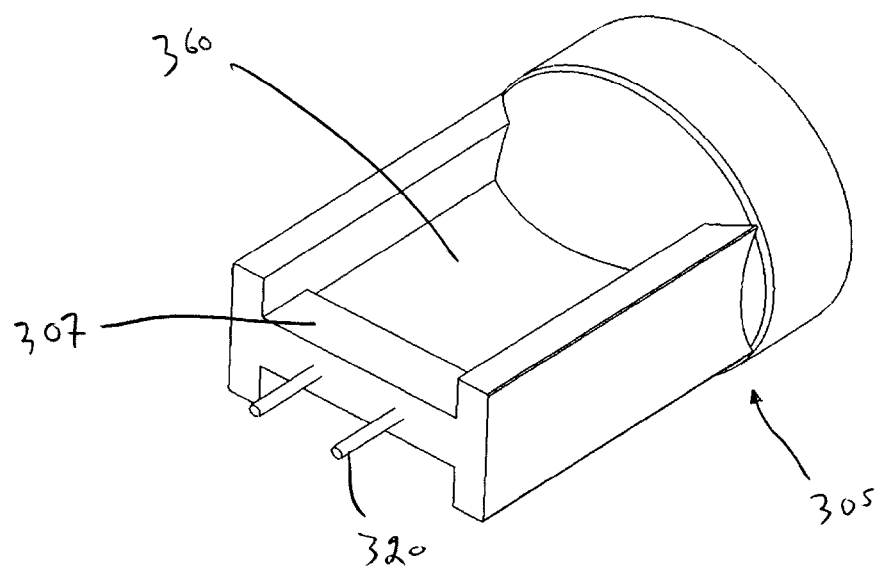

With initial reference to FIGS. 13 and 14, an insert element 305 is disposed near the end of lamp device 300. Insert element 305 (typically the pinch portion of the lamp) comprises a depression 306 and a step portion 307 on each side thereof.

Lamp device 300 has a filament 310 and a pair of electrical connectors 315 (only one is shown in FIG. 13) which is connected to a pair of electrical pins 320 emitting from insert 305. Electrical pins 320 are connected to electrical connector 315 by an electrical connection 317. Next, with reference to FIGS. 10 and 11, first half 325 of a base element is positioned such that insert 305 is seated in first half 325. Each of electrical pins 320 of insert 305 passes through a stop member 330 that is seated in first half 325.

On the marginal portions of first half 325 is disposed a pair of channels 335. Each channel 335 comprises a stop member 340 connected to each of a pair of return wires 345. As will be seen, each return wire 345 passes through a spring 350 disposed in channel 335. Spring 350 is chosen to achieve the same effect as spring 265 discussed above with reference to the embodiment shown in FIGS. 4-7.

Figure 9:
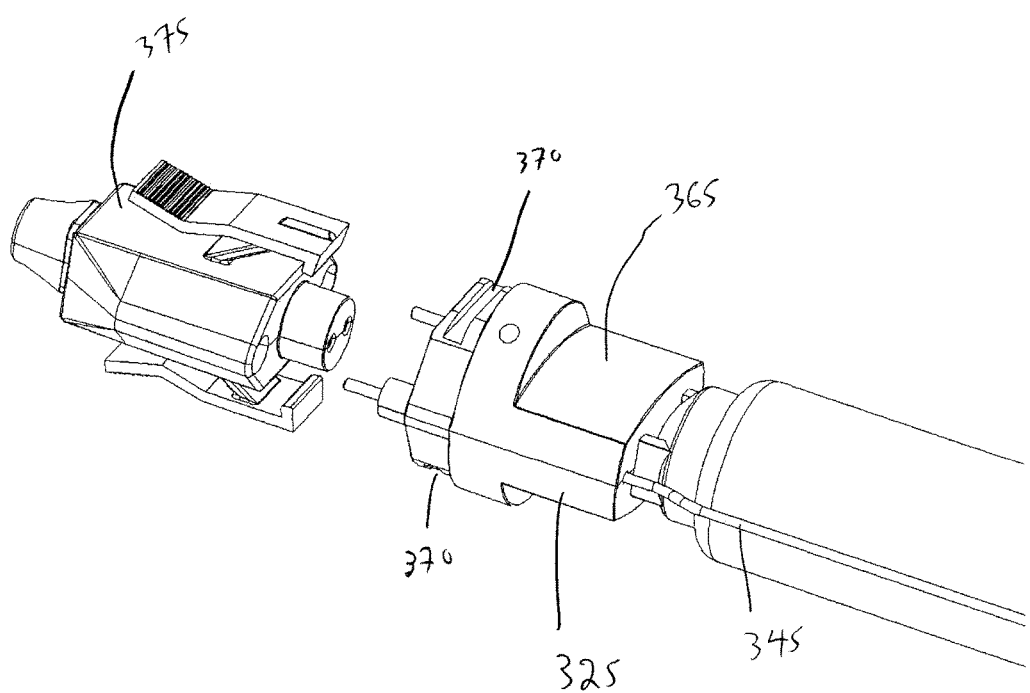
Figure 10:
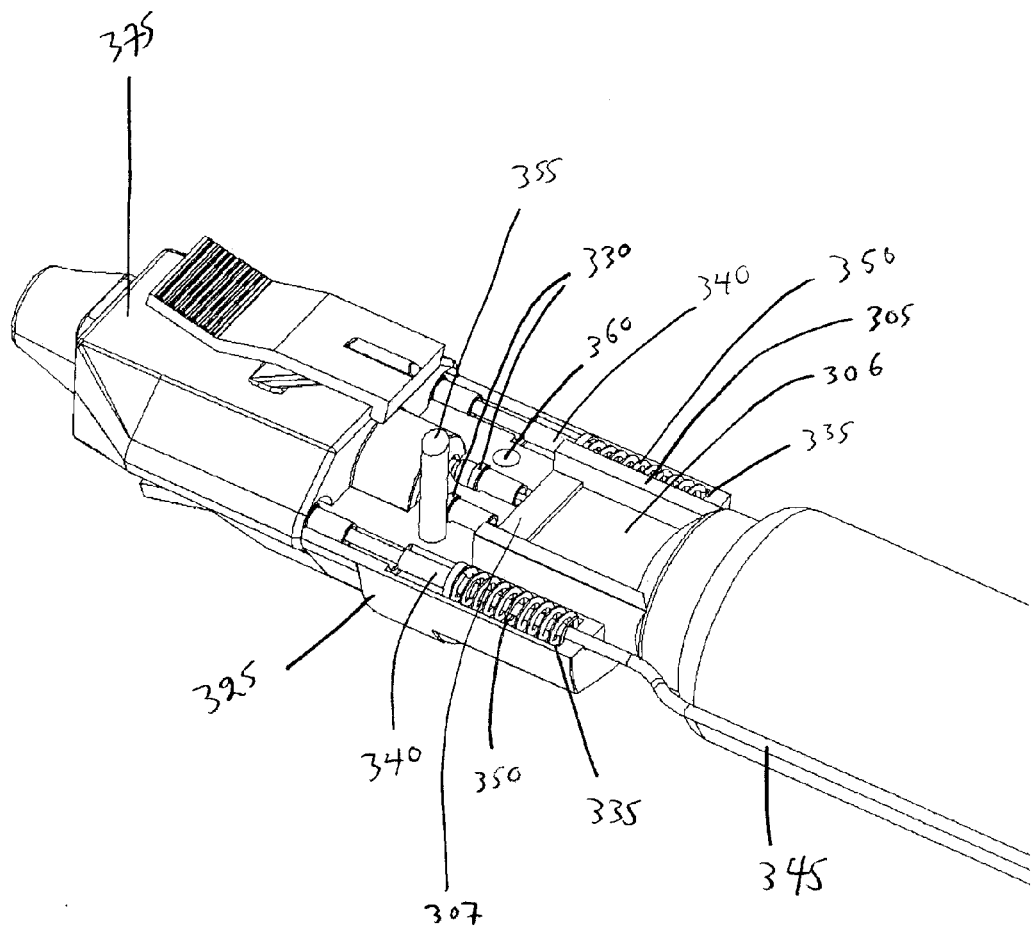
Figure 11:
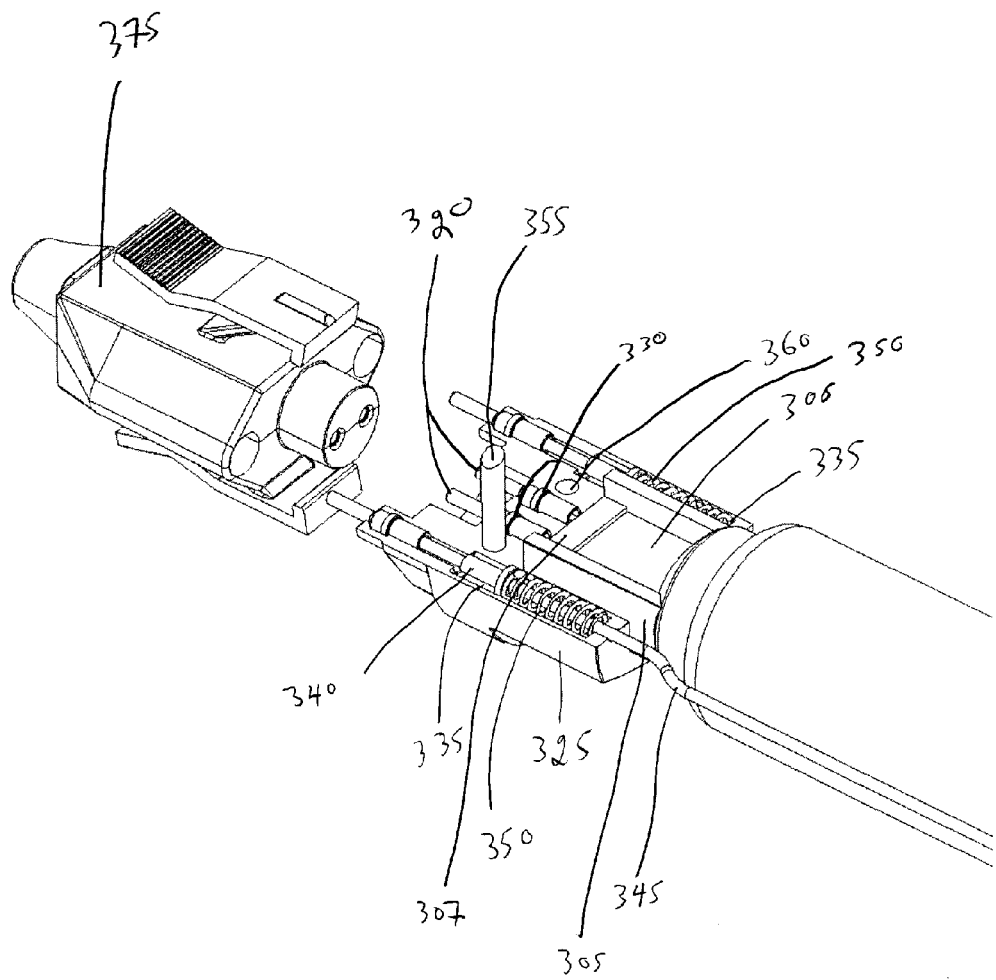
Figure 12:
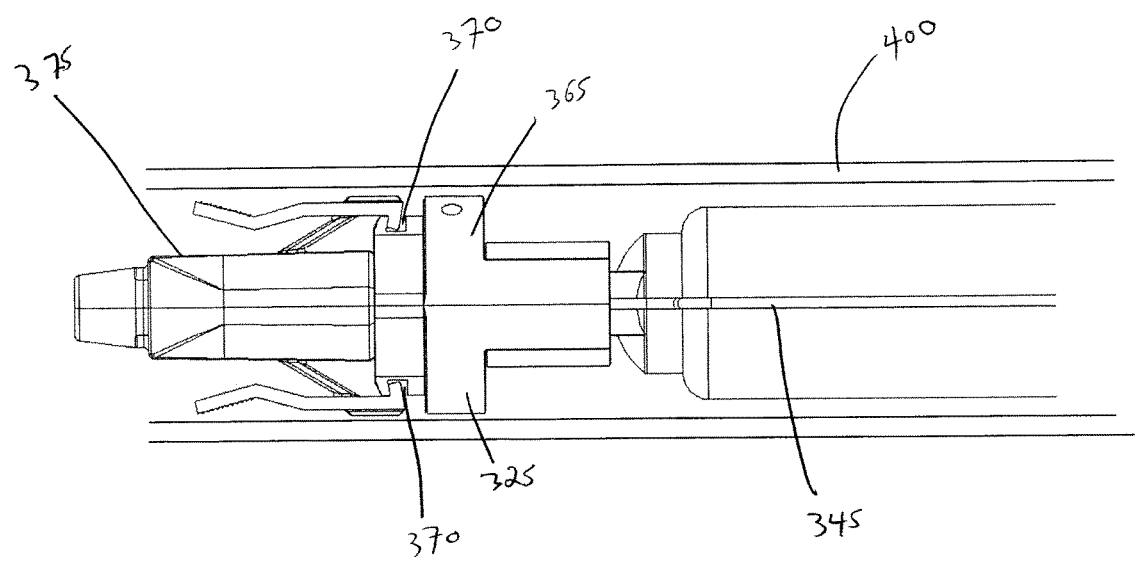

With reference to FIGS. 10 and 11, it will be seen that first half 325 comprises a post 355 and a receptacle 360. A second half 365 (FIG. 12) of the base unit is provided and has a mirror image design of first half 325. Second half 365 is disposed on first half 325 to complete the base unit as shown in FIG. 9. The completed base unit as shown in FIG. 9 comprises a pair of slots 370 on which may be clipped a plug connector 375. Plug connector 375 has electrical leads (not shown) connected to it which are, in turn, connected to a power supply (not shown). Disposition of the complete connection shown in FIG. 8 in a quartz sleeve 400 is shown in FIG. 12. As will be evident, the design of plug connector 375 is such that accidental disconnection of plug connector 375 from the completed base unit is not possible (i.e., there is not sufficient space within the confines of quartz sleeve 400 to allow plug connector 375 to disengage from the completed base unit).

Each of first half 325 and second half 365 are configuration to have an interior shape that is complementary to depression 306 and step portion 307 of insert element 305. This serves to engage insert element 305 to the assembled unit of first half 325 and second half 365.

Figure 15:
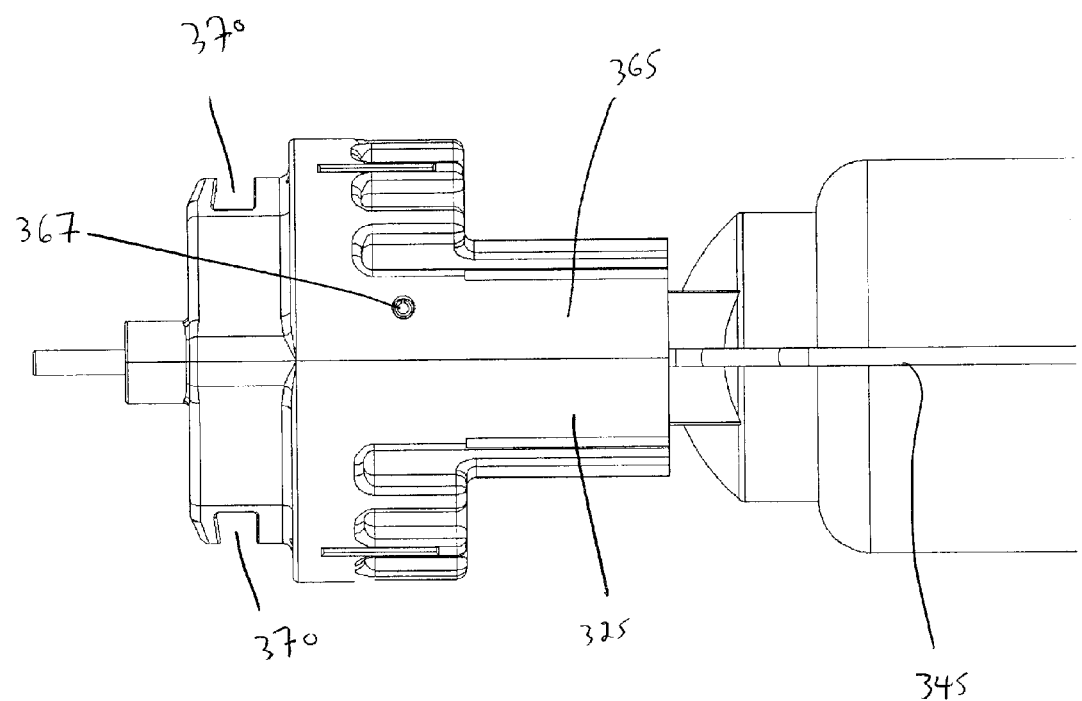

With reference to FIG. 15, there is shown the complete base unit. First half 325 and second half 365 are secured to one another by a roll (or split) pin 367 that is passed through an aperture 366 in first half 325 and an aperture (not shown) in second half 365.

Figure 16:
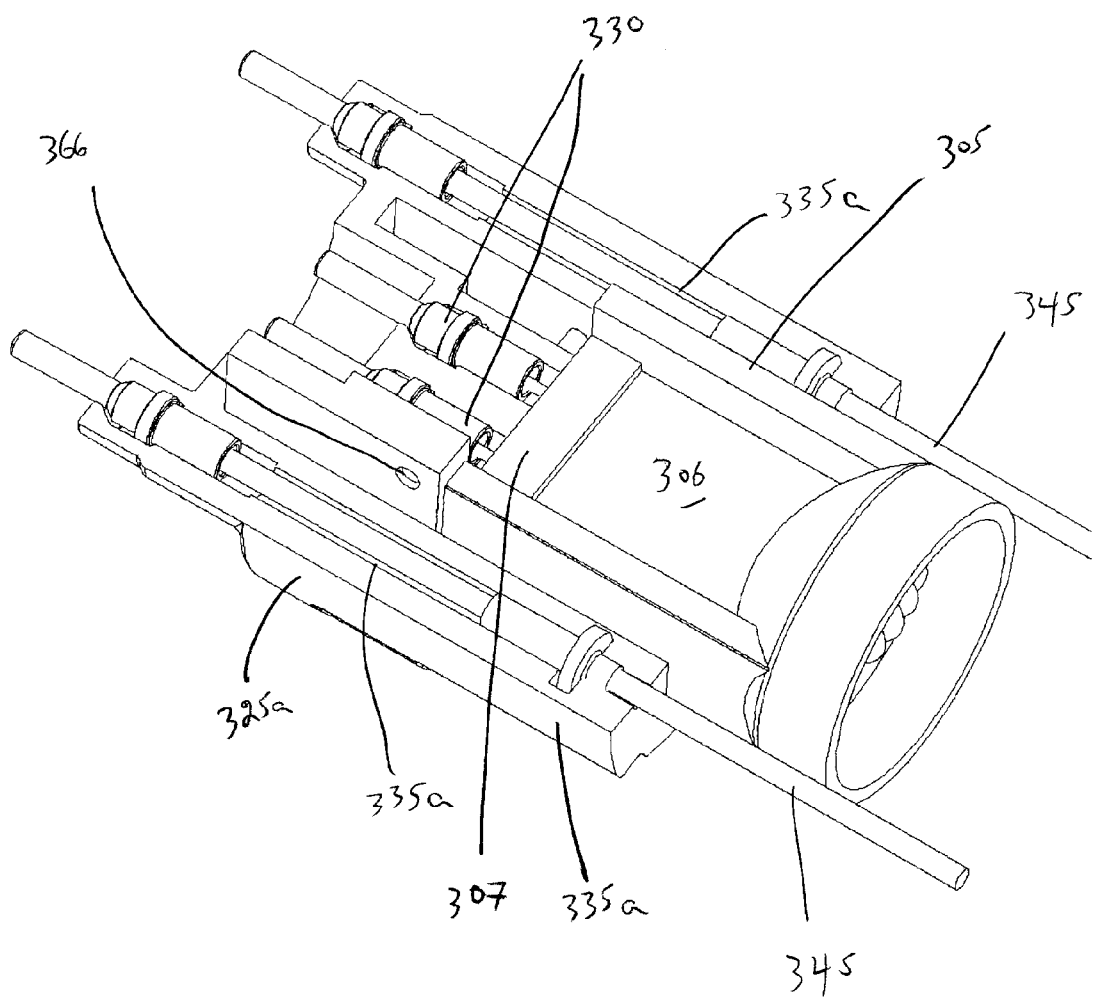
FIGS. 16-17 illustrate a third embodiment of the present lamp device.
Figure 17:
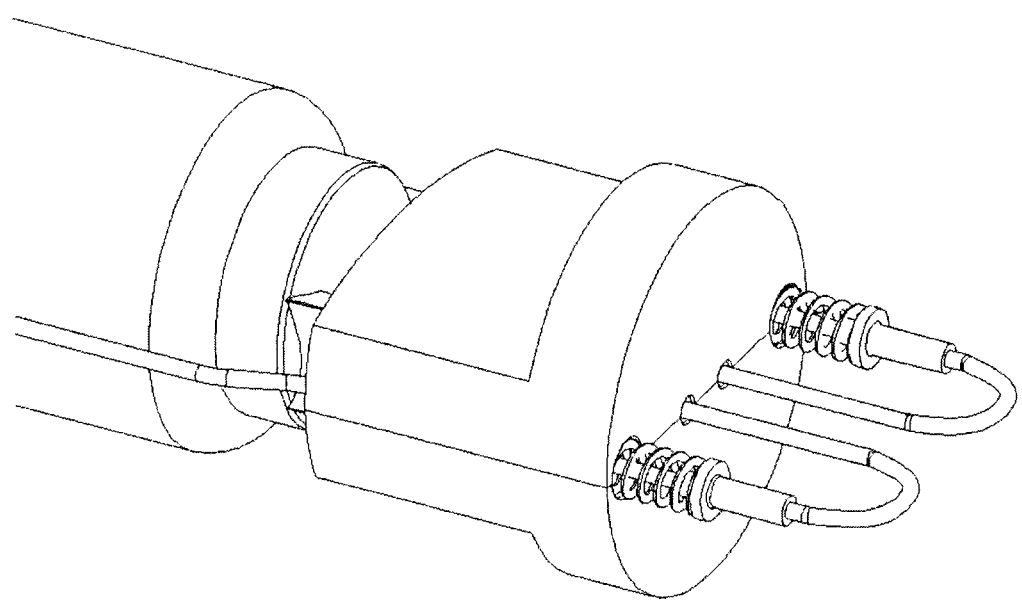

With reference to FIGS. 16 and 17, there is shown a slightly modified version of the embodiment shown in FIGS. 8-15. In this case, the tensioning function that was in channel 335 of first half 325 has been moved to the opposite end of the lamp and is shown, particularly, at FIG. 17.

With reference to FIGS. 18-22, there is illustrated a lamp device 400.

Lamp device 400 comprises a proximal end portion 410 and a distal end portion 420. A lamp cavity portion 430 is disposed between proximal end portion 410 and distal end portion 420. Lamp cavity portion 430 is conventional and, for example, may contain electrodes (not shown for clarity) or the like at or near proximal end portion 410 and distal end portion 420. The important point is that lamp cavity 430 is configured to emit radiation such as ultraviolet radiation.

Proximal lamp end portion 410 comprises a socket element 425. Connected to socket element 425 are a pair of support rods 427,429.

Proximal end portion 410 further comprises an elongate pinch portion 435 emanating from lamp cavity 430. As is known in the art, it is conventional to construct lamp cavity 430 from a radiation transparent material such as quartz. Preferably, this is also the material used for construction of elongate pinch portion 435. In a highly preferred embodiment, elongate pinch portion 435 is integral with lamp cavity 430.

Emanating from lamp cavity 430 are a pair of electrical leads 440,445. As illustrated particularly in FIG. 19, electrical lead 440 emanates from elongate pinch portion 435 and is connected to an electrode (not shown) disposed in the proximal region of lamp cavity 430. Preferably, elongate pinch portion 435 surrounds, more preferably encases, electrical lead 440.

Electrical lead 445 emanates from distal end portion 420 of lamp device 400. Electrical lead 445 is fed back toward proximal end portion 410 of lamp device 400.

Figure 18:
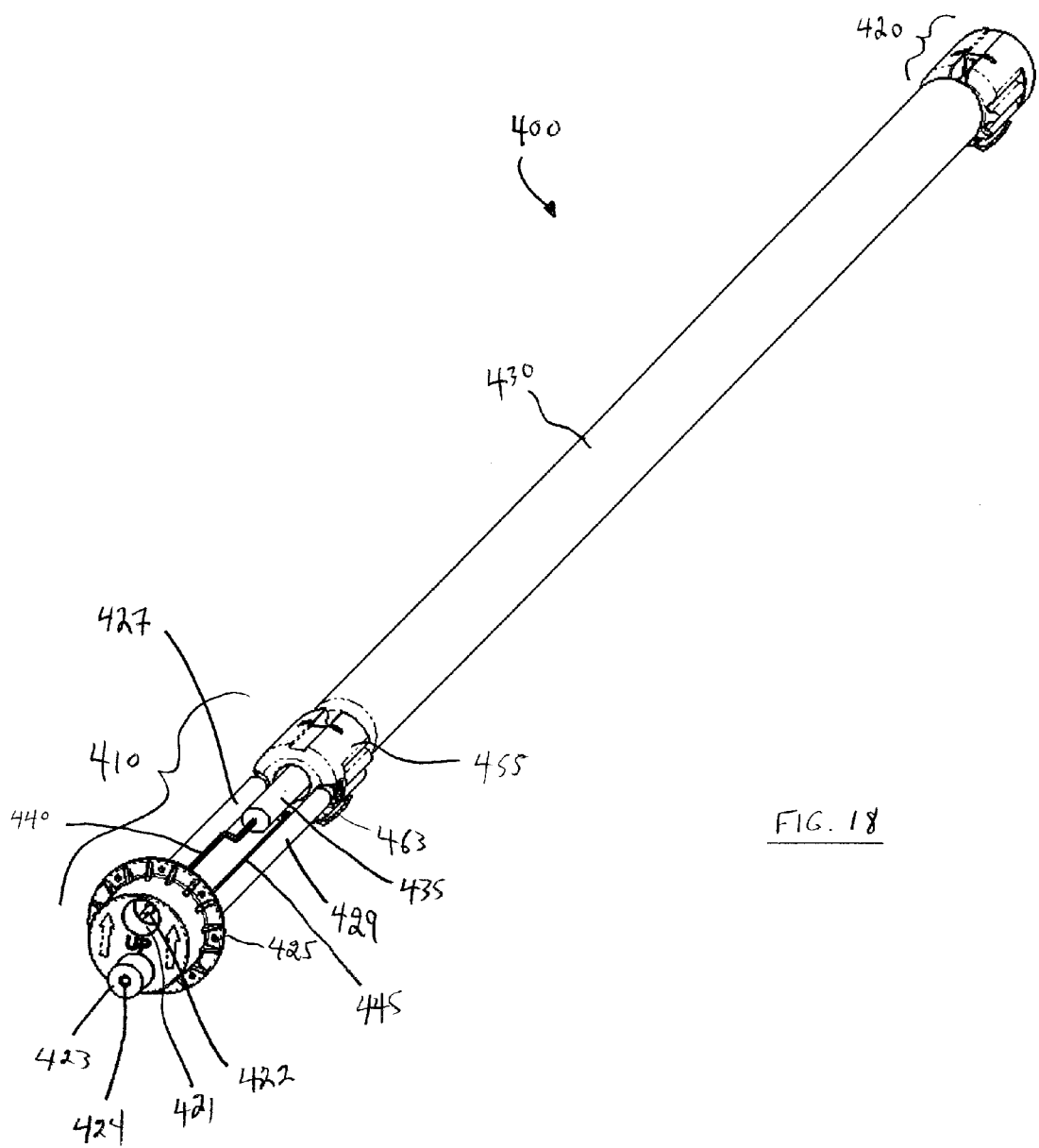
FIGS. 18-22 illustrate a fourth embodiment of the present lamp device.
Figure 19:
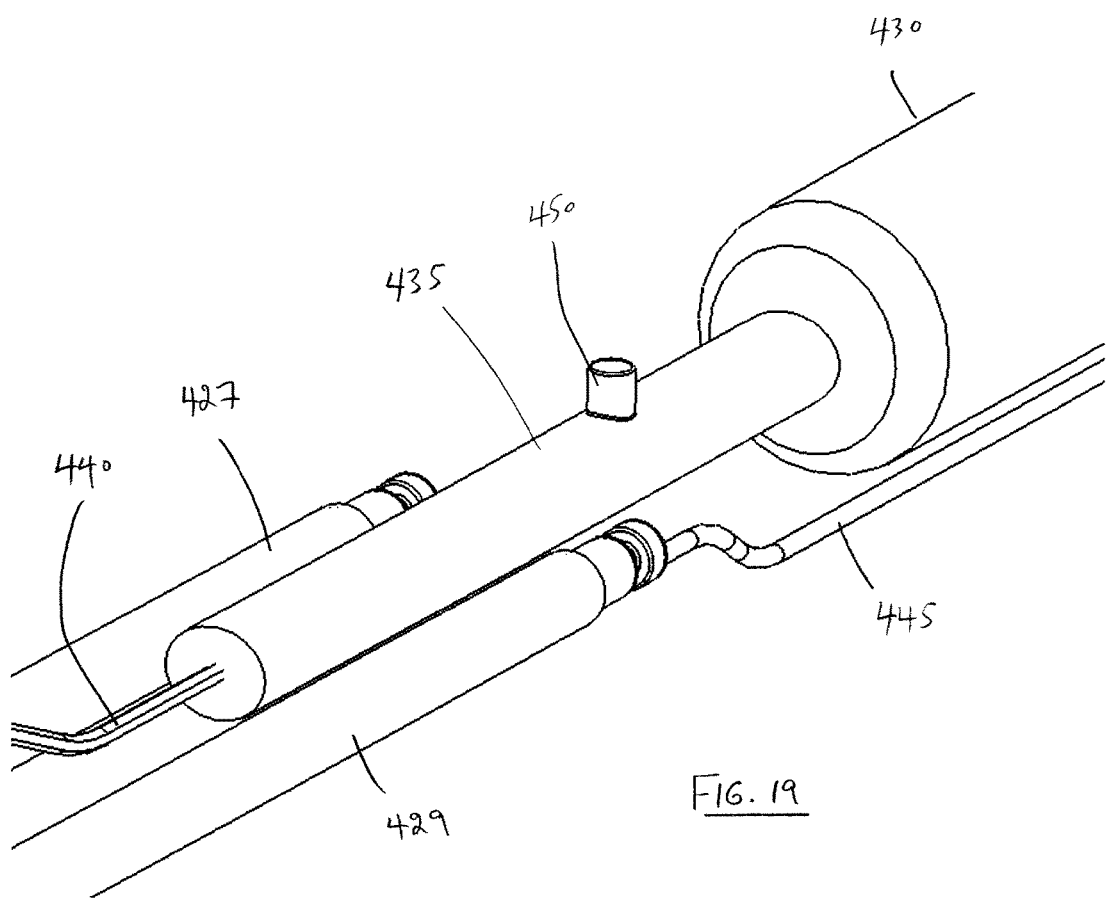

As shown in FIG. 18, socket 425 comprises a pair of electrical attachments to connect lamp device 400 to an electrical power supply (not shown). These electrical attachments are configured to be complementary to electrical attachments connected to the power supply (not shown).

Thus, socket 425 comprises a receptacle 421 having disposed therein a pin 422 connected to electrical lead 440.

Socket 425 further comprises a male member 423 having a receptacle 424 for receiving a complementary pin connector (not shown) from the power supply (not shown).

Disposed on elongate pinch portion 435 is a pin 450.

As shown in FIG. 18, proximal end portion 410 also comprises a base portion 455. As will be described in more detail below, base portion 455 serves to secure lamp cavity 430 to socket 425. Preferably, base portion 455 is made from a material capable of absorbing heat. For example, base portion 455 may be made from a ceramic material such as alumina. In a preferred embodiment, base portion 455 is constructed as a single piece base—e.g., using casting or other conventional techniques.

Figure 21:
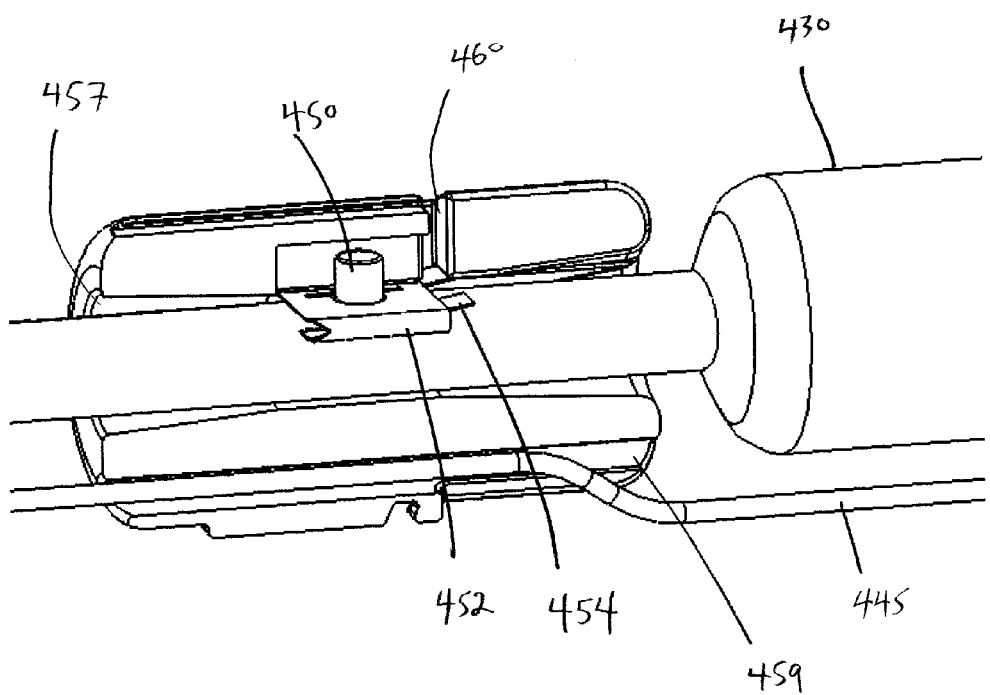
Figure 22:
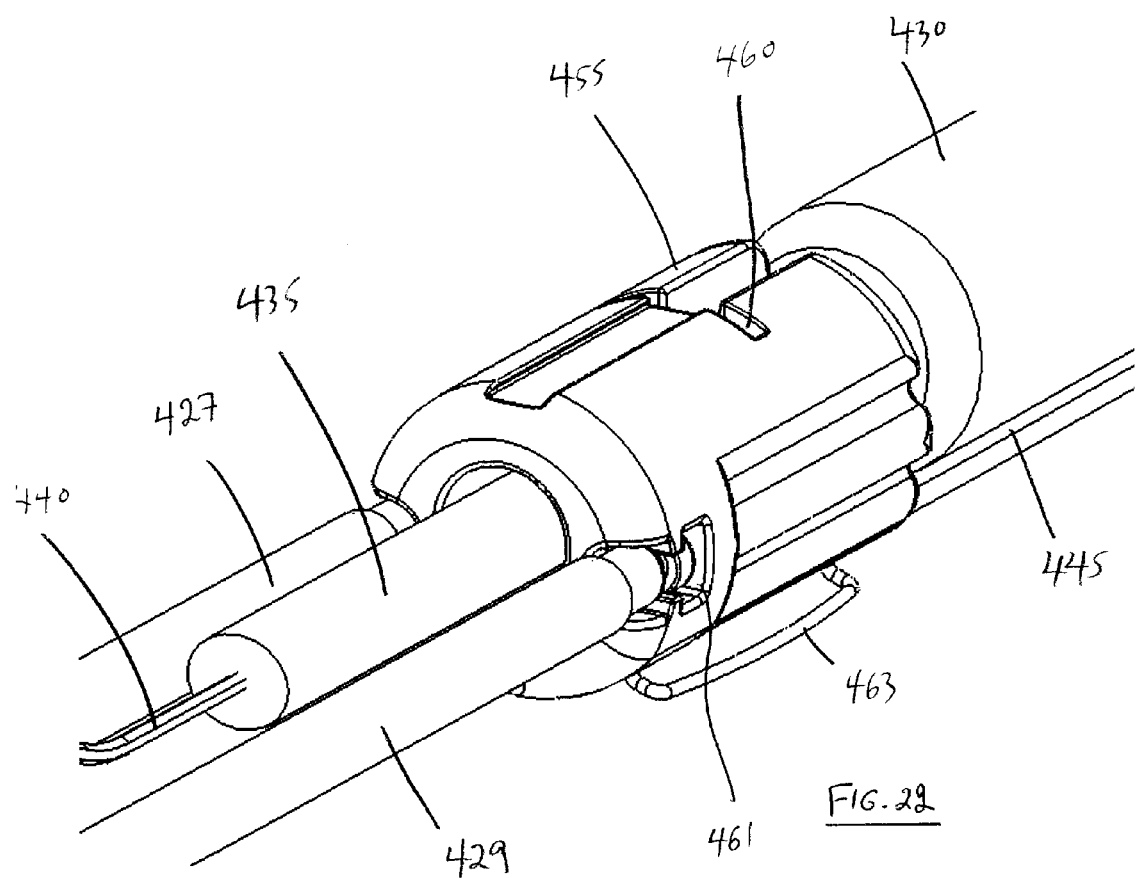

With particular reference to FIGS. 21 and 22, it can be seen that base portion 455 comprises a main passageway 457 through which elongate extension portion 435 may pass. Base portion 455 further comprises a secondary passageway 459 through which electrical lead 445 may pass.

Base portion 455 further comprises a slot 460 whose function will be described below.

Base portion 455 further comprises a pair of receptacle portions 461 for receiving the distal ends of support rods 427,429.

Finally, base portion 455 comprises a pair of wire support members 463 which are mechanically attached to base portion 455 in a conventional manner (not shown). Wire support member 463 serve to locate lamp device 400 in a quartz sleeve (not shown).

Figure 20:
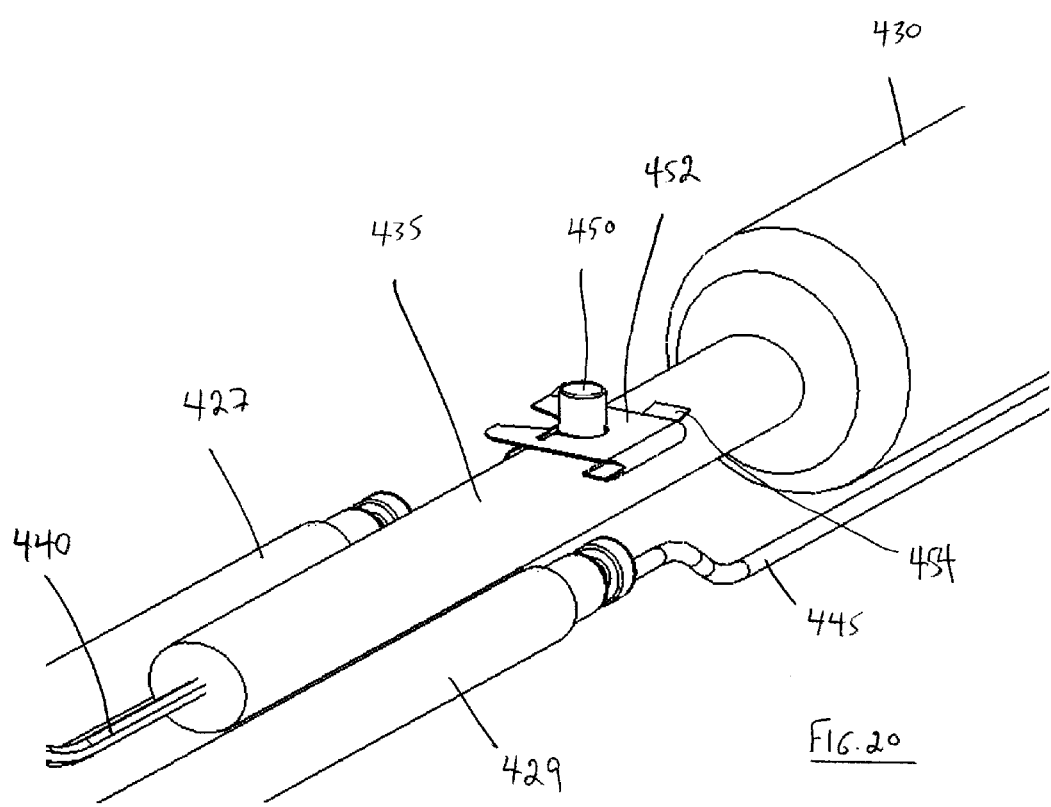

When it is desired to connect base portion 455 to lamp cavity 430, a clip portion 452 is disposed on pin 450—see FIG. 20. Clip portion 452 comprises a tab portion 454.

Base portion 455 is slid over the end of elongate extension portion 435 until tab portion 454 of clip portion 452 engages with slot 460 of body portion 455. At this point, body portion 455 is secured to lamp cavity 430. Clip portion 452 can be configured to be reversibly or irreversibly engageable to slot 460 of body portion 455.

Support rods 427,429 may then be inserted into and secured with respect to receptacle portions 461 of base portion 455—see FIG. 22.

Figure 23:
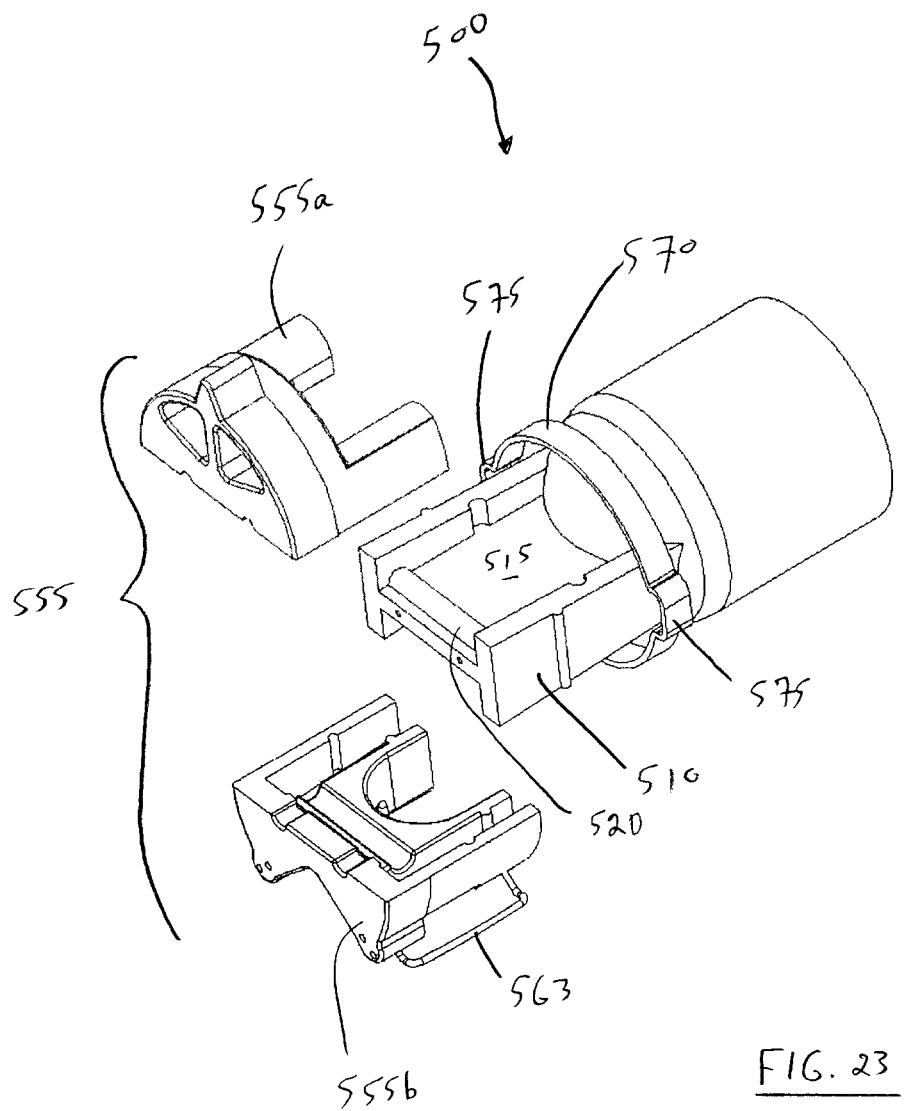
FIGS. 23-24 illustrate a fourth embodiment of the present lamp device.
Figure 24:
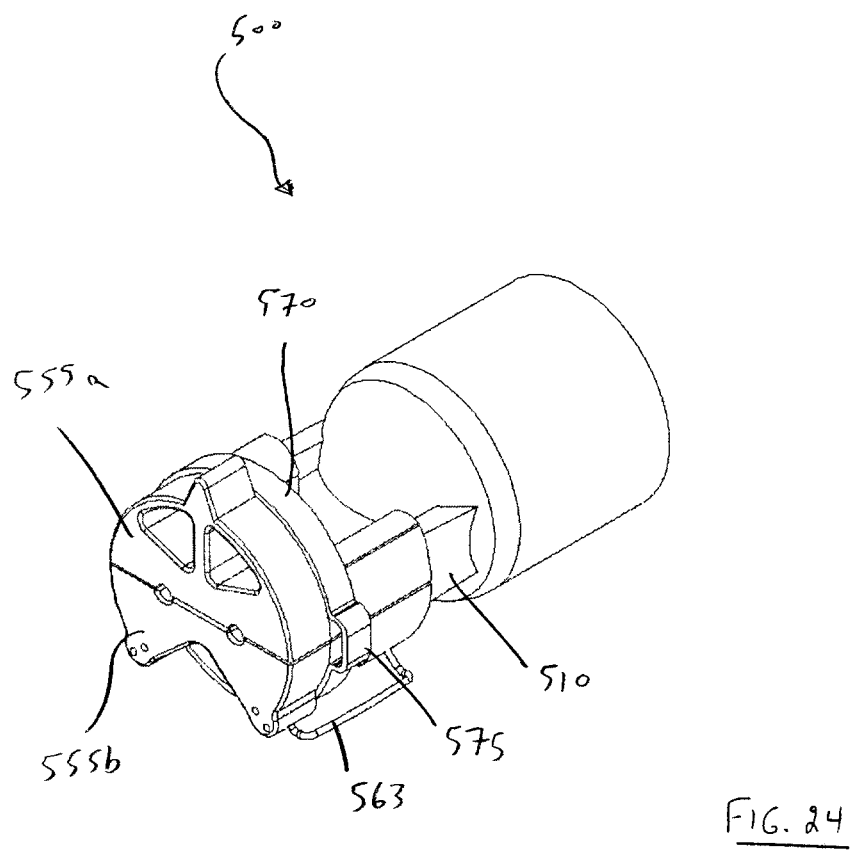

With reference to FIGS. 23-24, there is shown a lamp device 500.

Lamp device 500 comprises a pinch element 510 similar to the one described above with reference to FIG. 14. Pinch element 510 comprises a depression 515 and a step element 520.

A base unit 555 is provided and comprises a first base half 555a and a second base half 555b. The inside surfaces of base halves 555a,555b are configured such that they are complementary with depression 515 and step portion 520 of pinch element 510.

Base unit half 555b comprises a pair of wire support members 563 (only one is shown) which are mechanically attached to base unit half 555b and serve a function similar to that described above with reference to wire support members 563.

Also provided on pinch portion 515 is a tension ring 570 comprising a pair of tension tabs 575. When it is desired to connect base unit 555 to pinch portion 515, base unit halves 555a,555b are positioned around pinch portion 515. Next, each of tension tabs 575 of tension ring 570 are squeezed together thereby securing base unit halves 555a,555b together—the completed assembly is shown in FIG. 24.

Figure 25:
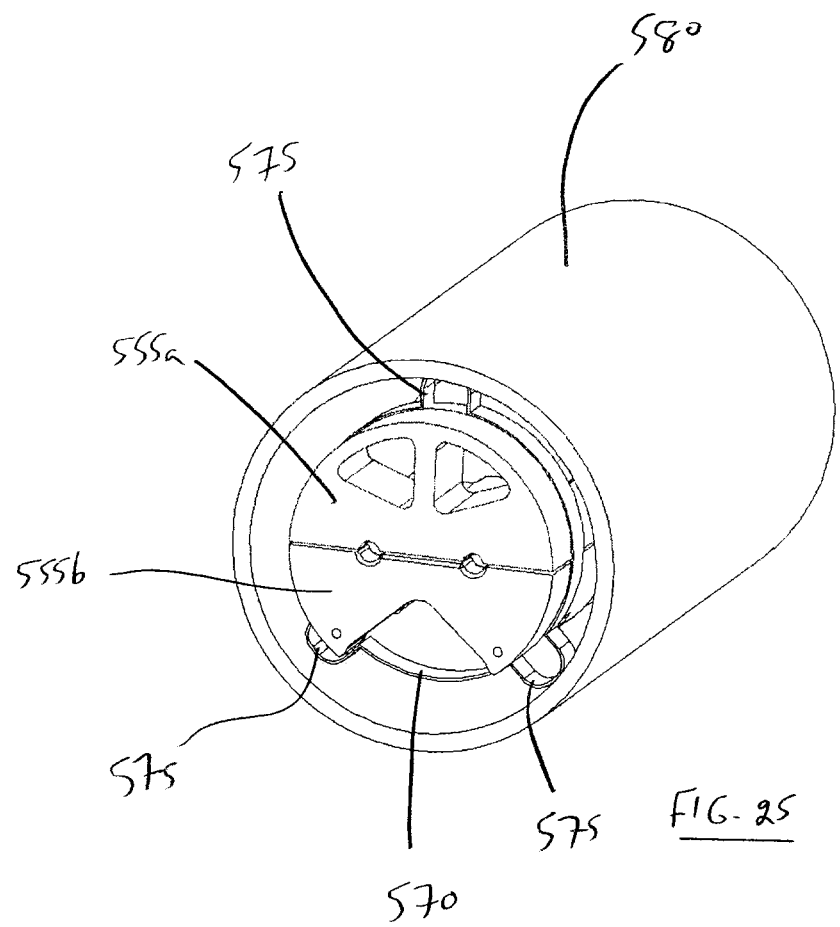
FIG. 25 illustrates a sixth embodiment of the present lamp device.

With reference to FIG. 25, there is a slight modification shown to lamp device 500. Specifically, wire support members 563 have been omitted and tension ring 570 comprises a trio of tension tabs 575. The provision of trio of tension tabs 575 serves to facilitate correct location of lamp device 500 in a quartz sleeve 580.

Figure 26:
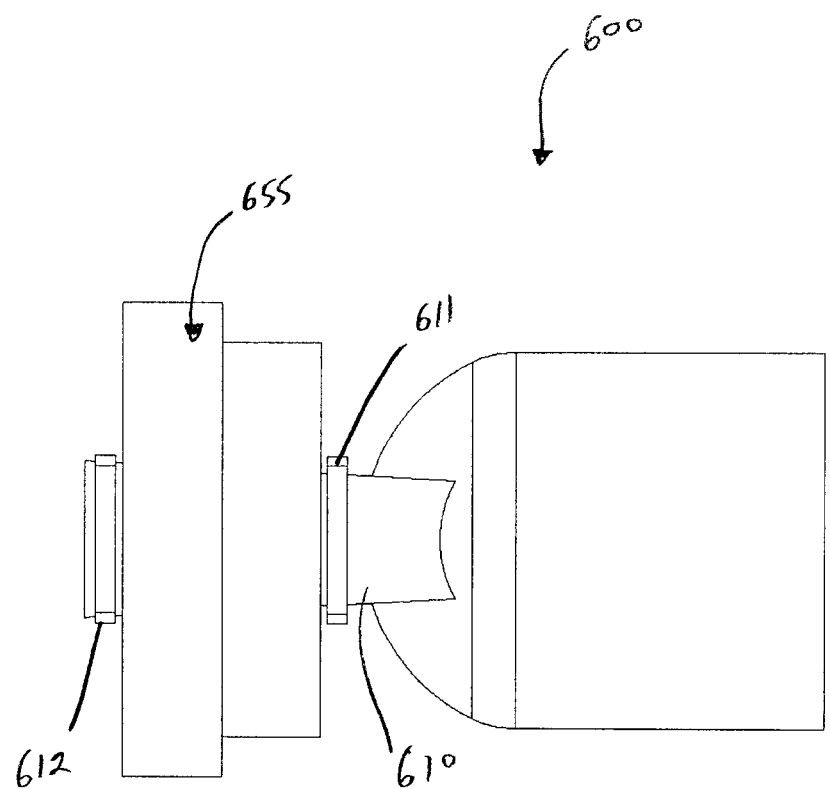
FIGS. 26-27 illustrate a seventh embodiment of the present lamp device.
Figure 27:
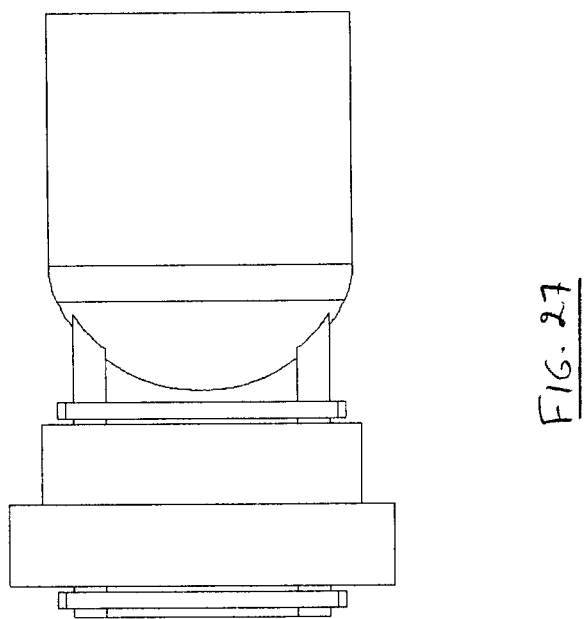

With reference to FIGS. 26-27, there is illustrated an end portion of a lamp device 600. FIG. 26 illustrates a side elevation of lamp device 600 and FIG. 27 illustrates a top view of lamp device 600.

Lamp device 600 comprises pinch portion 610 over which is disposed a unitary base portion 655 that is similar to base portion 455 discussed above. In this embodiment, base portion 455 is secured to pinch 610 by a pair of clips 611,612 which are placed under tension in a conventional manner so as to create a friction fit with pinch portion 610.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A radiation lamp comprising:
   an elongate radiation-emitting cavity having a longitudinal axis;
   a first electrical connection base disposed at a first end of the elongate radiation-emitting cavity;
   a second electrical connection base disposed at a second end of the elongate radiation-emitting cavity;
   a first elongate electrical connector and a second elongate electrical connector disposed in the first electrical connection base;
   an electrical lead electrically connecting one of the first elongate electrical connectors and a second elongate electrical connectors to the second electrical connection base; and
   a tensioning element, separate from the first and second electrical connectors, disposed on at least one of the first electrical connection base and the second electrical connection base, the tensioning element being configured to apply tension to the electrical lead between the first electrical connection base and the second electrical connection base in a direction that is: (i) substantially parallel to the cavity longitudinal axis, and (ii) away from the elongate radiation-emitting cavity.

2. The radiation lamp defined in claim 1, wherein the first electrical connection base comprises a first receptacle for receiving a portion of the first end of the elongate radiation-emitting cavity.

3. The radiation lamp defined in claim 2, further comprising a first locking portion for securing the first electrical connection base to the first end of the elongate radiation-emitting cavity.

4. The radiation lamp defined in claim 1, wherein the second electrical connection base comprises a second receptacle for receiving a portion of a second end of the elongate radiation-emitting cavity.

5. The radiation lamp defined in claim 4, further comprising a second locking portion for securing the second electrical connection base to the second end of the elongate radiation-emitting cavity.

6. The radiation lamp defined in claim 1, wherein a tensioning element disposed on each of the first electrical connection base and the second electrical connection base.

7. The radiation lamp defined in claim 1, wherein, the tensioning element comprises a biasing element.

8. The radiation lamp defined in claim 7, wherein the biasing element comprises a spring.

9. The radiation lamp defined in claim 1, comprising a pair of first elongate electrical connectors and a pair of second elongate electrical connectors.

10. The radiation lamp defined in claim 9, wherein the pair of first elongate electrical connectors and the pair of second elongate electrical connectors are substantially parallel with respect to one another.

11. The radiation lamp defined in claim 9, wherein the pair of first elongate electrical connectors and the pair of second elongate connectors are in a spaced relationship along the longitudinal axis.

12. The radiation lamp defined in claim 9, wherein the pair of first elongate electrical connectors and the pair of second elongate electrical connectors are aligned in a spaced relationship along the longitudinal axis.

13. The radiation lamp defined in claim 2, wherein the elongate radiation emitting cavity comprises an ultraviolet radiation-emitting cavity.

14. The radiation lamp defined in claim 9, wherein at least one of the pair of first elongate electrical connectors comprises a male portion of a male-female connection system.

15. The radiation lamp defined in claim 9, wherein each of the pair of first elongate electrical connectors comprises a male portion or a female portion of a male-female connection system.

16. The radiation lamp defined in claim 9, wherein at least one of the pair of second elongate electrical connectors comprises a male portion of a male-female connection system.

17. The radiation lamp defined in claim 9, wherein each of the pair of second elongate electrical connectors comprises a male portion of a male-female connection system.

18. The radiation lamp defined in claim 9, wherein the pair of the first elongate electrical connectors and the pair of the second elongate electrical connector each comprises a male portion of a male-female connection system.

19. The radiation lamp defined in claim 9, wherein one of the pair of first elongate electrical connectors and the pair of second elongate electrical connectors comprises a male portion of a male-female connection system and the other of the pair of first elongate electrical connectors and the pair of second elongate electrical connectors comprises a female portion of a male-female connection system.

20. The radiation lamp defined in claim 9, wherein at least one of the pair of second elongate electrical connectors comprises a female portion of a male-female connection system.

21. The radiation lamp defined in claim 9, wherein each of the pair of second elongate electrical connectors comprises a female portion of a male-female connection system.

22. The radiation lamp defined in claim 9, wherein the pair of the first elongate electrical connectors and the pair of the second elongate electrical connector each comprises a female portion of a male-female connection system.

* * * * *